(12) United States Patent
Kumar et al.

(10) Patent No.: US 11,787,755 B1
(45) Date of Patent: Oct. 17, 2023

(54) ISOMERIZATION PROCESS

(71) Applicant: UOP LLC, Des Plaines, IL (US)

(72) Inventors: Manoj Kumar, Gurgaon (IN); Avijit Basu, New Delhi (IN); Valentina Di Mauro, Surrey (GB)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/900,367

(22) Filed: Aug. 31, 2022

(51) Int. Cl.
*C07C 5/22* (2006.01)
*B01D 53/02* (2006.01)

(52) U.S. Cl.
CPC ............ *C07C 5/2206* (2013.01); *B01D 53/02* (2013.01); *B01D 2257/2064* (2013.01)

(58) Field of Classification Search
CPC ....... C07C 5/22; C07C 5/2206; C07C 5/2213; C07C 5/222; C07C 5/2226; C07C 5/2233; C07C 5/224; C07C 5/2246; C07C 5/2253; C07C 5/226; C07C 5/2266; C07C 5/2273; C07C 5/228; C07C 5/2286; C07C 5/2293; C07C 5/27; C07C 5/2702; C07C 5/2705; C07C 5/2708; C07C 5/271; C07C 5/2713; C07C 5/2716; C07C 5/2718; C07C 5/2721; C07C 5/2724; C07C 5/2727; B01D 53/02; B01D 2257/2064
See application file for complete search history.

(56) References Cited

U.S. PATENT DOCUMENTS

| | | | |
|---|---|---|---|
| 10,479,741 B2 | 11/2019 | Kumar | |
| 10,710,943 B1 | 7/2020 | Kumar | |
| 2016/0060191 A1* | 3/2016 | Kumar | ..................... C07C 7/00 585/800 |

* cited by examiner

*Primary Examiner* — In Suk C Bullock
*Assistant Examiner* — Jason Y Chong
(74) *Attorney, Agent, or Firm* — Paschall & Associates, LLC; Mark Goldberg

(57) ABSTRACT

A hydrocarbon isomerization system for an iC4 feed stream that provides for removal of C3s from an isomerization reactor feed stream by the addition of a depropanizer column to remove C3s from the reactor effluent stream after it has passed through a stabilizer column. This configuration prevents a buildup of C3s in the system and provides significant savings by reducing the size of the chloride treaters that are used to remove chlorides from off gas, increasing chlorides recovered to the hydrocarbon feed stream for use in combination with the isomerization catalyst. Significant utility savings are provided as well as a reduction in the amount of perchloroethane (PERC) and adsorbent that are required.

14 Claims, 1 Drawing Sheet

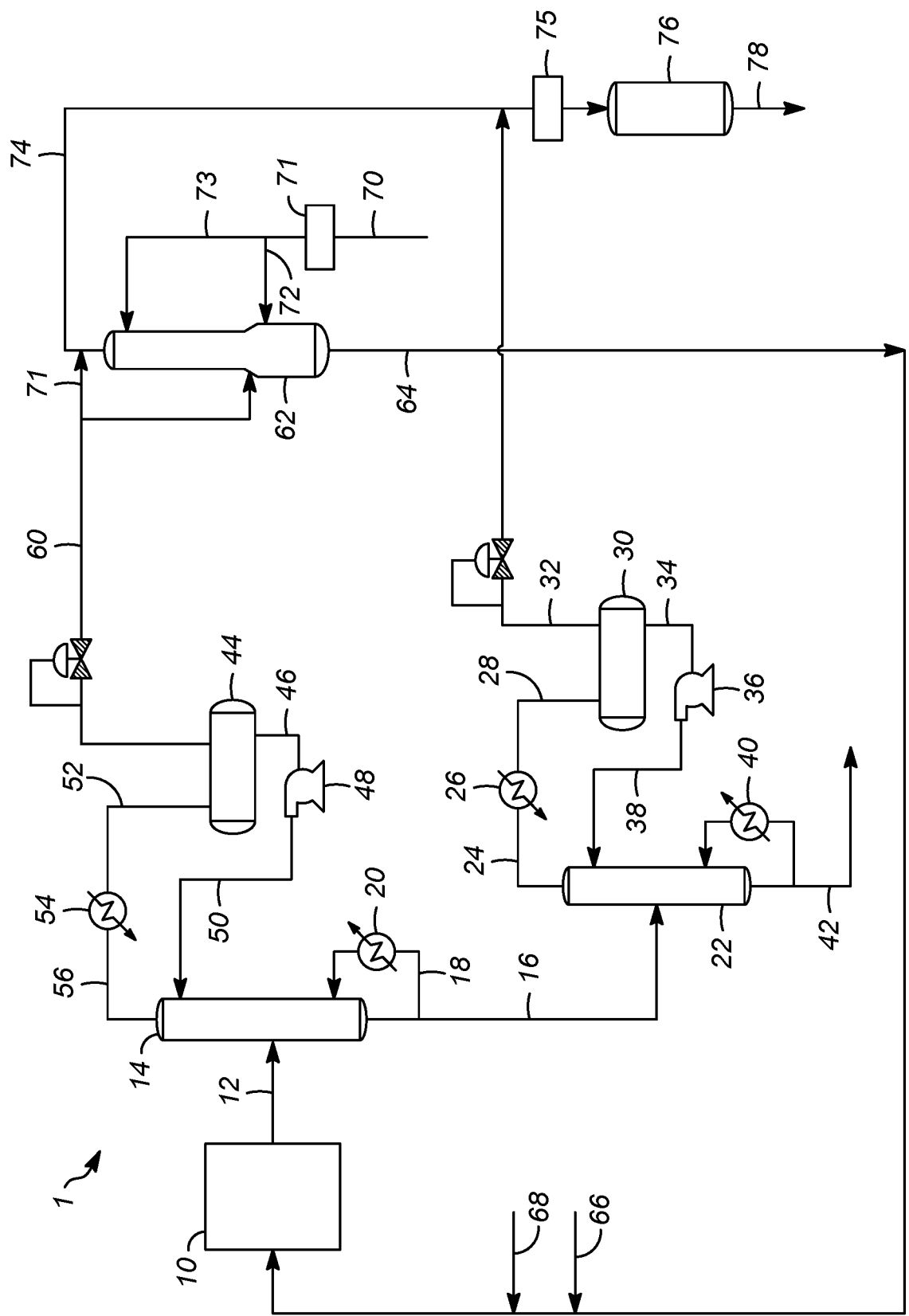

ISOMERIZATION PROCESS

FIELD

The subject matter of the present disclosure generally relates to processes and apparatus for isomerizing hydrocarbons and more particularly relates to minimizing chloride consumption and reduction in adsorbent quantity in a process and apparatus for isomerizing hydrocarbons.

BACKGROUND

Isomerization catalyst requires a continuous injection of chlorides to maintain the acid sites activity at a rate of 150 wppm of combined feed to isomerization reactors such as in UOP PENEX™ and BUTAMER™ processes. The chlorides injected to the isomerization reactors result in the presence of hydrogen chloride and/or other chlorinated compounds in the gaseous and liquid effluents obtained from the isomerization unit, which inevitably leads to corrosion of the facilities, formation of deposits or salts based on chlorine, or accelerated contamination of catalysts which might be located downstream of the isomerization unit. Thus, it is important to eliminate all traces of hydrogen chloride or other chlorinated compounds from these effluents.

Typically, such chlorides are scrubbed with a caustic solution in a net gas scrubber (NGS) before sending off gases to a fuel gas header or alternate destinations. This requires large amounts of caustic consumption on a continuous basis and refiners want to reduce the treatment cost of spent caustic. Caustic handling and treatment is an environmental concern and is cost intensive.

Alternatively, a portion of chlorides from the effluent stream could be recovered and recycled back by absorbing with feed stream as stated in U.S. Pat. Nos. 10,479,741 and 10,710,943. This reduces the chloride in reactor effluent making it feasible to replace caustic with chloride treaters using adsorbent. This still requires large amount of adsorbent for chloride removal and refiners prefer to reduce the quantity to reduce cost of fresh adsorbent as well as land filling post usage.

Therefore, there is a need for improved processes and apparatus for efficiently, handling the chlorine injected into the isomerization process and reducing net chloride consumption. Further. it is desirable to reduce the amount of adsorbent required for chloride treaters in the overall process, thereby decreasing associated costs. Other desirable features and characteristics of the present subject matter will become apparent from the subsequent detailed description of the subject matter and the appended claims, taken in conjunction with the accompanying drawings and this background of the subject matter.

In some current designs it has been found that under operating conditions of an isomerization reactor that there are a quantity of C3 hydrocarbons that end up in a stabilizer off gas stream and then to an absorber column. Almost all of the C3s from the absorber vapor feed stream are absorbed in the liquid feed stream which results in the accumulation of C3s in the loop formed by the reactor, stabilizer and absorber. This requires a larger fraction of stabilizer of gas stream bypassing the absorber column resulting in more chlorides going to chloride treaters and requiring large sized multiple chloride treaters.

SUMMARY system and process are provided for isomerizing a hydrocarbon feed stream comprising at least one of $C_4$ to $C_7$ hydrocarbons, wherein the process and process comprises isomerizing a first portion of the hydrocarbon feed stream in the presence of an isomerization catalyst and hydrogen in an isomerization reactor under isomerization conditions to produce an isomerized stream; stabilizing the isomerized stream in a stabilizer unit to provide a stabilizer off-gas stream comprising chlorides and a liquid isomerate stream; and sending the liquid isomerate stream to a depropanizer column to produce a C4 product stream and a C3 vapor stream. A first portion of a stabilizer off-gas stream may be sent to an absorber column to provide an absorber overhead stream and an absorber bottoms stream. A second portion of the stabilizer off-gas stream may be sent to a chloride treater. C3 vapor stream from the depropanizer column may be sent to a chloride treater. The absorber bottoms stream may be sent to the isomerization reactor. The hydrocarbon feed stream may be dried before being sent to the absorber column and isomerized in the isomerization reactor.

The C4 product stream may comprise normal C4 hydrocarbons. The hydrocarbon feed stream may comprise about 95-98% isobutanes. The stabilizer off-gas stream further comprises C2-hydrocarbons, hydrogen and chlorides. About 97-98% of the chloride may be sent from the absorber to the isomerization reactor. The stabilizer unit and the depropanizer column may each comprise about 30 trays.

About 95-98 of C3 hydrocarbons from the stabilizer bottoms stream are removed by the depropanizer. The stabilizer column may operate at a pressure of about 300-350 psig, temperature of about 90-120 F and a reflux to feed molar ratio of 0.5-1.5. The depropanizer column may operate at a pressure of about 150-200 psig, a temperature of about 90-120 F and a reflux to feed molar ratio of 0.5-1.5. The C3 vapor stream is sent from the depropanizer column to the chloride treaters. The chloride treaters remove chlorides and a net gas is produced.

There are a number of advantages that have been found to result from the present invention with the addition of the depropanizer column. These include a significant reduction in the need to introduce chlorides into the flow scheme with about a reduction in percholoroethylene (PERC) consumption of 70-80%. There is a similar reduction in the need for adsorbents with up to a 70-80% reduction that includes an advantage of reduced land filling costs and allows for the use of 2 chloride treaters in series to remove chlorides instead of 3 chloride treaters in previous designs. The reduction in equipment has a further advantage provided of reduction in overall utility costs of 30-35%. There is a significant reduction in the build-up of light ends with C3s reduced from about 8-10% to 1-3%. The addition of the depropanizer column allows for operational flexibility to handle higher levels of C3s in the feed and the possibility to create a separate C3 rich product stream, if required.

BRIEF DESCRIPTION OF THE DRAWINGS

The various embodiments will hereinafter be described in conjunction with the following drawing figures, wherein like numerals denote like elements, and wherein:

The FIGURE is a schematic diagram of a process and an apparatus for isomerizing hydrocarbons in accordance with an exemplary embodiment.

Skilled artisans will appreciate that elements in the FIGURE are illustrated for simplicity and clarity and have not necessarily been drawn to scale. For example, the dimensions of some of the elements in the FIGURE may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

The following detailed description is merely exemplary in nature and is not intended to limit the various embodiments or the application and uses thereof. Furthermore, there is no intention to be bound by any theory presented in the preceding background or the following Processes and apparatus for isomerizing hydrocarbons are provided herein. The process comprises isomerizing at least a portion of a hydrocarbon feed stream comprising at least one of C4 to C7 hydrocarbons in the presence of an isomerization catalyst and hydrogen under isomerization conditions to produce an isomerized stream. The isomerized stream is stabilized in a stabilizer to provide a stabilizer off-gas stream and a liquid isomerate stream. The liquid isomerate stream from the stabilizer bottoms comprises of C3+ and is sent to a depropanizer column to produce a C4+ product stream and a C3 vapor stream. The stabilizer off gas stream comprises of C2−, hydrogen and chlorides. At least a portion of the stabilizer off-gas stream is contacted with an exchange stream to provide an absorber overhead stream and absorber bottoms stream comprising chlorides. The absorber bottoms stream is passed to the isomerization reactor. The exchange stream may be a portion of the hydrocarbon feed-stream to the isomerization reactor or a side draw from the Deisobutanizer r column located downstream of the isomerization reactor. Absorber overhead stream, stabilizer off gas stream bypassing absorber and depropanizer vapor stream are combined, passed through a heater to increase temperature to 120-160 deg F and then to chloride treaters to remove residual chlorides to produce net gas stream.

As depicted, process flow lines in the FIGURE can be referred to, interchangeably, as, e.g., lines, pipes, branches, distributors, streams, effluents, feeds, products, portions, catalysts, withdrawals, recycles, suctions, discharges, and caustics.

As used herein, the term "unit" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "vapor" can mean a gas or a dispersion that may include or consist of one or more hydrocarbons.

As used herein, the term "stream" can include various hydrocarbon molecules and other substances. Moreover. the term "stream comprising Cx hydrocarbons" can include a stream comprising hydrocarbon with "x" number of carbon atoms, suitably a stream with a majority of hydrocarbons with "x" number of carbon atoms and preferably a stream with at least 75 wt % hydrocarbon molecules, respectively, with "x" number of carbon atoms. Moreover, the term "stream comprising Cx+ hydrocarbons" can include a stream comprising a majority of hydrocarbon molecules, with more than or equal to "x" carbon atoms and suitably less than 10 wt % and preferably less than 1 wt % hydrocarbon molecules, with x−1 carbon atoms. Lastly, the term "Cx—stream" can include a stream comprising a majority of hydrocarbon molecules with less than or equal to "x" carbon atoms and suitably less than 10 wt % and preferably less than 1 wt % hydrocarbon molecules, with x+1 carbon atoms.

As used herein, the term "overhead stream" can mean a stream withdrawn at or near a top of a vessel, such as a column.

The term "column" means a distillation column or columns for separating, one or more components of different volatilities. Unless otherwise indicated, each column includes a condenser on an overhead of the column to condense the overhead vapor and reflux a portion of an overhead stream back to the top of the column. Also included is a reboiler at a bottom of the column to vaporize and send a portion of a bottom stream back to the bottom of the column to supply fractionation energy. Feeds to the columns may be preheated. The top pressure is the pressure of the overhead vapor at the outlet of the column. The bottom temperature is the liquid bottom Gullet temperature. Overhead lines and bottom lines refer to the net lines from the column downstream of the reflux or reboil to the column.

As used herein, the term "bottoms stream" can mean a stream withdrawn at or near a bottom of a vessel, such as a column.

As used herein, the term "substantially" can mean an amount of generally at least about 90%, preferably about 95%, and optimally about 99%, by mole, of a compound or class of compounds in a stream.

An exemplary embodiment of the process and apparatus for isomerizing hydrocarbons is addressed with reference to a process and apparatus 1 according to an embodiment as shown in the FIGURE.

A hydrocarbon feed stream 70 includes at least one of C4 to C7 hydrocarbons. At least a portion of the hydrocarbon feed stream 70 is passed to an upper zone of absorbing vessel 62 and a second portion of the hydrocarbon feed stream is shown entering a lower portion of the absorbing vessel. In the absorbing vessel 62, the hydrocarbon feed stream 70 absorbs chlorides from a gaseous stream 60. In the system of the present invention, almost all of the overhead stream 60 from the stabilizer column 14 is sent to absorber column 62 with about 97-98% of the stream entering the absorber column and about 2-3% bypassing the absorber column to be combined with an absorber column overhead stream 74.

In the FIGURE, a chloride rich hydrocarbon feed stream 64 exits absorber vessel 62 and is sent to isomerization reactor 10, which comprises one or more reactors.. As shown, a make-up hydrogen gas 66 and a chloride compound 68 such as hydrogen chloride or perchloroethylene may be introduced to the chloride rich hydrocarbon feed stream 64, and the chloride rich hydrocarbon feed stream 64 may be heated in one or more heat exchangers, not shown, an isomerization reactor 10. The reactor 10 includes a suitable isomerization catalyst and is operated under isomerization conditions suitable to isomerize hydrocarbons from the chloride rich hydrocarbon feed stream 64 and provide an isomerized effluent 12.

The isomerized effluent 12 is passed to a stabilizer unit 14. Separation of the isomerized effluent 12 is carried out in the stabilizer unit 14 to provide a stabilizer off-gas stream 60 comprising chlorides and a liquid isomerate stream 16 containing C3+ hydrocarbons.

The liquid isomerate 16 is passed to a depropanizer column 22. A depropanizer overhead stream 24 containing C3 and lighter hydrocarbons is cooled in heat exchanger 26 and stream 28 passes to vessel 30 with C3 stream 32 sent to absorber overhead stream 74 to be first heated by heat exchanger 75 to about 150 F to increase gas velocity and then is treated by chloride treaters 76 with a net gas 78 exiting the bottom of chloride treaters 76. A heavier stream 34 comprising C4 hydrocarbons exits vessel 30 and is pumped by pump 36 with stream 38 returning to depropanizer column 22 as a reflux. The depropanizer column may have 30 trays as does the stabilizer column 14. A mixed C4+ product stream exits as a bottom stream 42 from depropanizer column 22 and a portion of the product stream may be heated in heat exchanger 40 and returned to depropanizer column 22. In this embodiment, it has been found that two chloride treaters operating in series are adequate to remove the chlorides from the net gas stream. The chloride treaters may have a smaller capacity than in the prior art systems.

Returning to the stabilizing column 14, the stabilizer off-gas stream 60 comprises chlorides that are to be removed and recycled to the isomerization reactor 10. Accordingly, the stabilizer overhead vapor stream 56 is cooled by heat exchanger 54 and cooled stream 52 is sent through vessel 44 with a vapor stream 60 comprising C2−, H2 and chlorides going to absorber 62. A heavier stream 46 comprising C3-C4 hydrocarbons exits vessel 44 and is pumped by pump 48 with stream 50 returning to stabilizer column 14 as a reflux.

An iC4 feed 70 is dried by dryer 71 and split into streams 72 and 73 that enter into absorber vessel 62. As mentioned above, within the absorbing vessel 62, the chloride compounds from the stabilizer off-gas stream 60 containing a mixture of C2−, H2 and HCl are absorbed by contact with a dried hydrocarbon feed stream 70 and returned to the isomerization reactor 10 in the chloride rich hydrocarbon feed stream 64. TABLE 1 below, shows summary data from process simulations based on the principles of the present invention which indicates that some of the significant advantages of the addition of the depropanizer column to the system as described below.

There are a number of advantages that have been found to result from the present invention and the addition of the depropanizer column. These include a significant reduction in the need to introduce chlorides into the flow scheme with about a reduction in percoloroethylene (PERC) consumption of 70-80%. There is a similar reduction in the need for chloride removal adsorbents with up to a 70-80% reduction that includes an advantage of reduced land filling costs in addition to the cost of fresh adsorbent and allows for the use of 2 chloride treaters in series to remove chlorides instead of 3 chloride treaters in series in previous designs. The reduction in equipment has a further advantage provided of reduction in overall utility costs of 30-35%. There is a significant reduction in the build-up of light ends with C3s reduced from about 8-10% to 1-3%. The addition of the depropanizer column allows for operational flexibility to handle higher levels of C3s in the feed and the possibility to create a separate C3 rich product stream, if required.

EXAMPLE

A comparison was made between the prior art system that had about 88% of the stabilizer off-gas stream passing to the absorber column and the new system that had about 97% of the stabilizer off-gas stream passing to the absorber column as well as a stabilizer column with fewer trays. A depropanizer column prevents the buildup of C3s in the process.

TABLE

| Parameter | Prior configuration | New Configuration |
|---|---|---|
| HCl recovery wt % | 88.0 | 97.06 |
| PERC injection MT/year | 3.52 | 0.86 |
| Stabilizer pressure psig | 290 | 320 |
| Stabilizer Trays | 50 | 30 |
| Stabilizer reboiler duty MW | 2.51 | 0.87 |
| Depropanizer pressure psig | Not Applicable | 175 |
| Depropanizer Trays | Not Applicable | 30 |
| Depropanizer reboiler duty MW | Not Applicable | 0.96 |
| Number of chloride treaters | 3 | 2 |
| Chloride treater size mm × mm | 1300 × 10500 | 900 × 9500 |

The invention claimed is:

1. A process for isomerizing a hydrocarbon feed stream comprising at least one of $C_4$ to $C_7$ hydrocarbons, wherein the process comprises:
   drying the hydrocarbon feed stream to provide a dried hydrocarbon feed stream;
   absorbing chlorides from a gaseous stream with the dried hydrocarbon feed stream in an absorber column to provide a chloride rich hydrocarbon feed stream and a chloride lean vapor;
   isomerizing the chloride rich hydrocarbon feed stream in the presence of an isomerization catalyst and hydrogen in an isomerization reactor under isomerization conditions to produce an isomerized stream;
   stabilizing the isomerized stream in a stabilizer unit to provide a stabilizer off-gas stream comprising C2– hydrocarbon, $H_2$ and chlorides, and a liquid isomerate stream;
   sending said liquid isomerate stream to a depropanizer column to produce a C4+ product stream and a C3 vapor stream; and
   sending a first portion of the stabilizer off-gas stream as the gaseous stream to the absorber column to provide an absorber overhead stream comprising the chloride lean vapor and an absorber bottoms stream comprising the chloride rich hydrocarbon feed stream.

2. The process of claim 1 wherein a second portion of said stabilizer off-gas stream is sent to a chloride treater bypassing the absorber column.

3. The process of claim 2 wherein said C3 vapor stream is sent from said depropanizer to said chloride treater.

4. The process of claim 2 wherein the absorber overhead stream, the second portion of the stabilizer off-gas stream and the C3 vapor stream are combined, passed through a heater to increase in temperature to 120-160° F. and then sent to the chloride treater.

5. The process of claim 1 wherein the absorber bottoms stream is sent to the isomerization reactor.

6. The process of claim 1 wherein said C4 product stream comprises normal C4 hydrocarbons and C5 hydrocarbons.

7. The process of claim 1 wherein said hydrocarbon feed stream comprises about 95-98% isobutane.

8. The process of claim 1 wherein said stabilizer unit operates at a pressure of about 300-350 psig, a temperature of about 90-120° F. and a reflux to feed ratio of 0.5-1.5.

9. The process of claim 1 wherein about 97-99.9% of said chlorides is sent from said absorber column to said isomerization reactor.

10. The process of claim 1 wherein said stabilizer unit comprises about 30 trays.

11. The process of claim 1 wherein said depropanizer column comprises about 30 trays.

12. The process of claim 1 wherein about 95-98% of the C3 hydrocarbons present in the said liquid isomerate stream are removed by said depropanizer.

13. The process of claim 1 wherein said depropanizer operates at a pressure of about 150-200 psig, a temperature of about 90-120° F. and a reflux to feed ratio of 0.5-1.5.

14. The process of claim 1 wherein said chloride treater removes chlorides and produces a net gas.

\* \* \* \* \*